(12) United States Patent
Foser et al.

(10) Patent No.: US 6,250,926 B1
(45) Date of Patent: Jun. 26, 2001

(54) METHOD FOR PRODUCING DENTAL REPLACEMENT

(75) Inventors: Hanspeter Foser, Balzers (LI); Gerard Ubassy, Impasse des Ormeaux (FR)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 09/427,916

(22) Filed: Oct. 27, 1999

Related U.S. Application Data

(60) Provisional application No. 60/112,242, filed on Dec. 14, 1998.

(30) Foreign Application Priority Data

Nov. 2, 1998 (DE) ............................................. 198 50 451

(51) Int. Cl.[7] .............................. A61C 5/08; A61C 13/08
(52) U.S. Cl. ........................... 433/218; 433/219; 433/226
(58) Field of Search .................................... 433/218, 219, 433/226, 228.1, 204, 212.1, 203.1

(56) References Cited

U.S. PATENT DOCUMENTS

| 3,761,728 | * | 9/1973 | Kochavi | 148/3 |
| 4,879,136 | * | 11/1989 | Polz | 433/207 |
| 5,346,397 | * | 9/1994 | Braiman | 433/223 |

* cited by examiner

Primary Examiner—Nicholas D. Lucchesi
(74) Attorney, Agent, or Firm—Alan S. Korman; John C. Thompson

(57) ABSTRACT

In the method for manufacturing a dental replacement a dental support structure is provide that has a labial and a buccal side. A fired, pre-shaped ceramic part is placed onto the labial or the buccal side and at least partially embedded in a ceramic paste. Subsequently, the thus assembled dental replacement is fired.

19 Claims, 1 Drawing Sheet

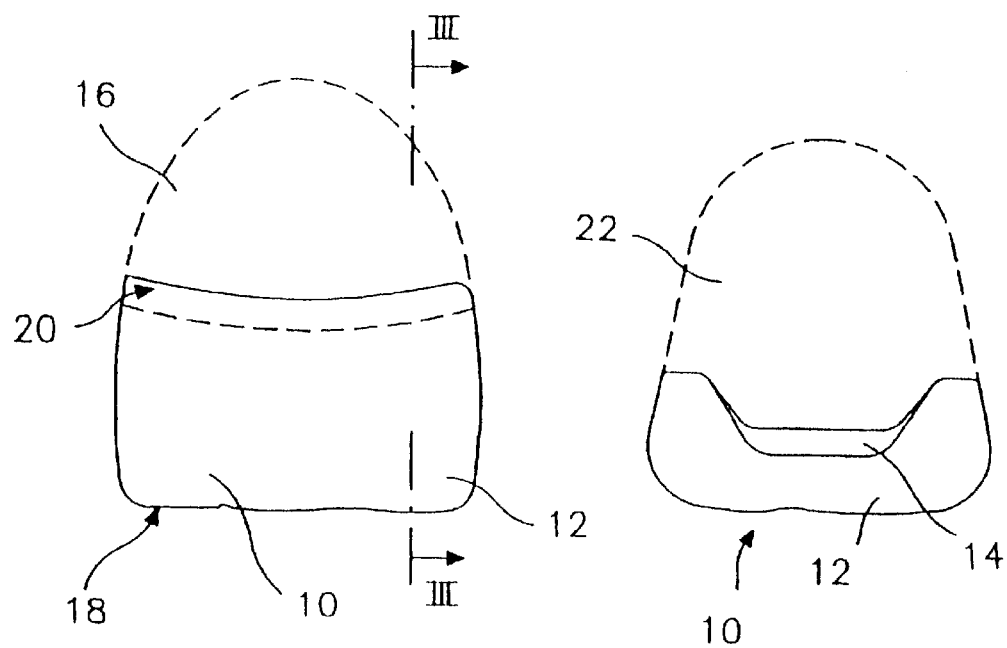
Fig. 1
Fig. 2
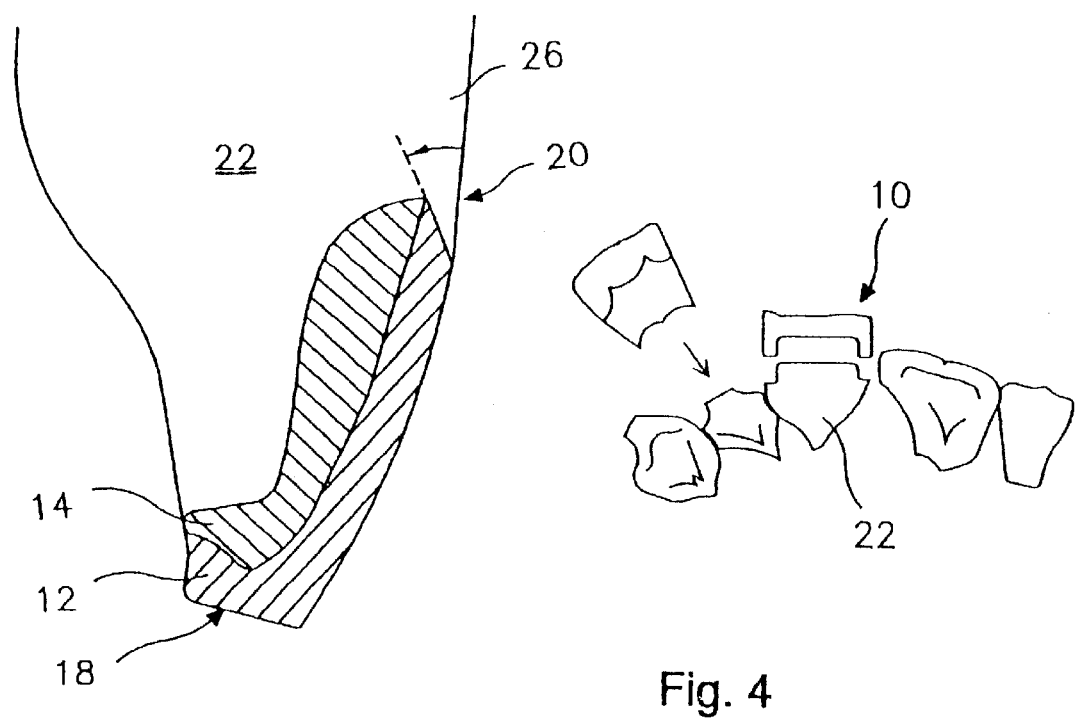
Fig. 3
Fig. 4

METHOD FOR PRODUCING DENTAL REPLACEMENT

This application claim benefit to Provisional Application Ser. No. 60/112,242 filed Dec. 14, 1998.

BACKGROUND OF THE INVENTION

The present invention relates to method for producing dental replacements wherein a pre-shaped ceramic part is applied to a dental support structure or a tooth stump model by a ceramic paste. The invention also relates to the dental replacement having a pre-shaped ceramic part that is connected by a ceramic paste to a dental support structure or a tooth stump model.

Such a method and such a dental replacement are known from German Offenlegungsschrift 36 04 059. A dental crown according to this publication is produced by first manufacturing a hollow cap and placing the hollow cap with the aid of a mineral dentin replacement material onto a tooth stump, i.e., a tooth stump model. The excess material which is pressed out by pressing the cap onto the tooth stump is removed or shaped and, subsequently, the assembly is fired. This solution is based on the known method of producing porcelain hollow crowns which are connected by tooth cement to the tooth stump model whereby instead of the tooth cement the mineral dentin replacement material is used for connecting the hollow cap to the tooth stump. This is designed to reduce the layer thickness of the hollow cap and to thus improve the esthetic appearance.

The manufacture of hollow caps according to German Offenlegungsschlinfs 36 04 059, however, has been difficult and has shown to be disadvantageous in practice. For example, a plurality of hollow caps with respective color, size, and shape of the desired tooth replacement must be premanufactured and stored so that it is necessary to have an extensive hollow cap supply in storage. On the other hand, the esthetic result is not satisfactory because the external shape of the replacement tooth is always a standard result. The coloration can not accommodate the differentiation of natural teeth even when, for example, the supply of 100 different hollow caps is provided which is necessary for five different colors, five different shapes and four different front teeth.

In contrast, pre-shaped ceramic parts have the advantage that the shaping of the tooth replacement can be individualized while, in contrast, it is essentially predetermined for hollow caps.

Since the hollow cap method has not found acceptance, it has also been suggested to apply multiple ceramic support layers onto a dental support structure or a tooth stump model in sequence in order to allow for an individualized esthetic appearance that closely resembles a natural tooth. The layers can be produced in the dental lab according to an impression. This, for example, known from U.S. Pat. No. 4,473,353 according to which a corresponding layer is applied with an acrylic adhesive after a respective impression has been prepared.

A similarly adhesively connected hollow cap is also known from U.S. Pat. No. 4,813,874. This method also includes producing an impression and does not employ premanufacture so that the work expenditure is relatively great.

It is therefore an object of the present invention to provide a method for producing dental replacements as well as a dental replacement of the aforementioned kind which provides an esthetically pleasing inexpensive tooth restoration which can be produced quickly.

SUMMARY OF THE INVENTION

This object is inventively solved by applying a fired, pre-shaped ceramic part onto the labial or buccal side of the tooth replacement so that it is at least partially embedded or enveloped by a ceramic paste.

The invention provides the advantage of using an embedded fired pre-shaped ceramic part. This is applied to the labial or buccal side of the tooth stump and is embedded at least partially by a ceramic paste. This inventive solution insures that individualization that is made possible by modeling and coloration of a ceramic paste, is realizable despite premanufacture of the ceramic part. On the other hand, it is no longer required to apply a plurality of ceramic layers in a sequential order and to fire each ceramic layer separately so that the work expenditure in the dental lab is greatly reduced.

In this context it is especially favorable when one or multiple, preferably two-layer, ceramic parts are used. Such a two-layer ceramic part is very similar to the translucence of natural teeth and is partly visible since it is at least partially embedded by the ceramic paste. This allows for a great simplification of the generally required layer technique on the visible labial or buccal side, which, has usually a curved (bulging) exterior shape, i.e., instead the application of the pre-shaped fired ceramic part is possible. It is understood that, in principle, a matching fired and pre-shaped ceramic part can also be used at the lingual side, whereby, on the one hand, the esthetic requirements in this area are less stringent and, on the other hand, since the exterior shape for molars is slightly convex and in the incisor area even concave, less material is required.

Inventively, it is suggested that the support structure which is comprised of a metal alloy is covered by an opaquing agent, and the support structure together with the opaquing agent are fired together. The opaquing agent has a higher melting temperature than the ceramic part and the ceramic paste so that it remains solid at the firing temperatures for the ceramic part as well as for the ceramic paste.

Onto the opaquing agent, which has a surface that has good adhesive properties, the ceramic paste is applied in excess and then the pre-shaped ceramic part is pressed onto the labial or the buccal side. Onto the pre-shaped ceramic part the same ceramic paste is then applied and shaped or modeled whereby this additional application already corresponds to the application of the last layer in the layering technique.

The finish-modeled dental replacement is then fired. Accordingly, with the inventive method the manufacture and individual firings of the first, second, and third ceramic layers can be produced with one single firing. It is understood that it may be expedient to employ the conventional painting technology, in the same manner as in the layering technique, whereby the coloration is individualized and, subsequently, a further firing process is undertaken.

Inventively, it is especially advantageous that the employed ceramic materials for the ceramic paste as well as for the pre-shaped ceramic part are compatible. Accordingly, there is hardly any difference or no difference at all in the heat expansion coefficient of the pre-shaped ceramic part and the ceramic paste so that there is no risk of crack formation.

Furthermore, the dental technician must not be especially trained for use of the inventive ceramic parts. The application of individual layers, is has been used in the past, requires considerable experience, while the method of the present invention can be easily performed by a less experienced dental technician which in the end is beneficial in regard to the quality of the dental replacement.

It is especially advantageous that the ceramic part is industrially pre-manufactured of two or more layers. It is only necessary to provide sets of small numbers, for example, three each for the incisor and the molar area of the jaw. These ceramic parts can be integrated anatomically and esthetically such into the ceramic paste that after firing a transition between the fired ceramic paste and the pre-shaped fired ceramic part can no longer be detected. The ceramic part is inventively partially imbedded in the ceramic paste and is thus integrated into the dental support structure. Its surface is preferably such that the surrounding ceramic paste will adhere well thereto which is also beneficial with regard to the stability of the dental replacement part.

At a firing temperature between 660° and 950° c., the ceramic pastes and the ceramic parts can be fired together such that no special requirements with regard to the selection of the firing furnace must be complied with. It is instead possible to employ the conventional furnaces for producing metal ceramics.

BRIEF DESCRIPTION OF THE DRAWINGS

The object and advantages of the present invention will appear more clearly from the following specification in conjunction with accompanying drawings, in which:

FIG. 1 is a schematic representation of one embodiment of the inventive ceramic part viewed from the labial side;

FIG. 2 shows the ceramic part according to FIG. 1 viewed from the lingual side;

FIG. 3 shows a section of the embodiment according to FIG. 1 along the line III—III of FIG. 1;

FIG. 4 shows the application of the inventive ceramic part onto the dental support structure in a view from the incisal side.

DESCRIPTION OF PREFERRED EMBODIMENTS

The present invention will be described in detail with the aid of several specific embodiments utilizing FIGS. 1–4.

The ceramic part 10 represented in FIG. 1 is embodied of two layers. The layer 12 facing the labial side is comprised of enamel while the layer 14 facing the lingual side is comprised of dentin. The represented embodiment refers to a ceramic part for an upper incisor 16 while it is understood that corresponding ceramic parts can also be used for other teeth such as bicuspids and optionally molars.

The ceramic part 10 covers, is can be seen in FIG. 1, almost the entire visible area of the incisor 16 on the labial side. At the transition portion 20 between the dental support structure and the pre-shaped ceramic part, the ceramic part is embedded in the ceramic paste so that the connection is essentially seamless and invisible.

As can be seen in FIG. 2, the ceramic material of the layer 14, which corresponds to dentin, is completely enclosed by the ceramic material that forms the enamel which is applied as layer 12. When viewed in a lingual view, the incisal area is covered by the ceramic part while the metal support structure 22 at the lingual side must not be provided with a ceramic part but is, in general, covered by the opaquing agent.

The design of the ceramic part and the connection to the metal support structure 22 can be seen especially well in FIG. 3. The layer 12 extends from the incisal area 18, following the curvature of a natural tooth, down toward the root area and ends at the transition portion 20 where it is pointed. In this transition area the layer 12 is covered by the ceramic paste 26 whereby overlap extends over an area of slightly less than 1 mm. The overlap angle is 15° to 75°, preferably 20° to 45°, and more preferred 30°.

Between the dental support structure 22 and the layer 12, the layer 14 of ceramic material that embodies the translucence of dentin is provided. This layer 14 is slightly thicker at the transitional portion 20 and extends to the lingual side across the support structure 22.

For manufacturing the inventive dental replacement, the metal support structure 22 is produced from a precious metal alloy according to conventional criteria. Onto the metal crown a ceramic opaquing agent is then applied and fired. It covers the metal color and encloses the support structure at the top side and the lateral surfaces completely. Subsequently, a ceramic paste is applied to the opaquing agent with conventional methods but is not yet fired. A two-layer translucent pre-shaped ceramic part is then pressed into the ceramic paste. This intermediate product is then positioned on a silicone support and the ceramic part together with the ceramic paste is then modeled and finished to a crown.

The crown is then removed from the silicone support and fired. The fired crown is finemachined. Optionally, ceramic corrections are applied before it is fired again. After completion of the crown by grinding the final coating is applied and fired.

The crown has then a tooth-like translucence and, even though the ceramic part is not completely embedded in the ceramic paste, it is not visible to the eye.

In this context it is especially advantageous when the transition portion is slanted in the aforementioned manner. By properly selecting the transition angle, it can be prevented that light refraction will make the ceramic part visible through the transition portion of the fired ceramic paste.

FIG. 4 shows in which manner the ceramic parts are placed onto the support structure 22. The ceramic parts 10 can clamp onto the labial side of the support structure 22 so that with such a clamping action form-locking and thus stable anchoring is provided.

What is claimed is:

1. A method for manufacturing a dental replacement, comprising the steps of:

a) providing a dental support structure having a labial or buccal side, and providing a fired pre-shaped ceramic part;

b) applying at least one layer of colored ceramic paste onto the labial or buccal side of the support structure;

c) pressing the fired pre-shaped ceramic part into the ceramic paste on the labial or buccal side; and d) firing together the fired pre-shaped ceramic part and the ceramic paste to form a dental replacement.

2. A method according to claim 1, further including the step of:

applying an opaquing agent to the dental support structure and firing the dental support structure together with the opaquing agent before said step b).

3. A method according to claim 2, further including the step of selecting the ceramic paste to have a melting temperature that is lower than the melting temperature of the opaquing agent.

4. A method according to claim 1, wherein the pre-shaped ceramic part ends before an incisal edge, a medial edge, and a distal edge of the dental replacement.

5. A method according to claim 4, wherein the incisal edge, the medial edge, and the distal edge are sculpted from a ceramic material.

6. A method according to claim 1, wherein the pre-shaped ceramic part is embedded into the ceramic paste at least partially such that the pre-shaped ceramic part is well integrated into the ceramic paste and not completely covered by the ceramic paste.

7. A method according to claim 1, wherein the pre-shaped ceramic part is selected from a set of fired, pre-shaped ceramic parts of varying sizes such that the selected pre-shaped ceramic part is a size smaller than a pre-shaped ceramic part having a matching size for the desired labial or buccal side.

8. A method according to claim 1, wherein the incisal edge, the distal edge and the medial edge of the pre-shaped ceramic part are pointed.

9. A method according to claim 1, further including the step of at least partially covering the fired pre-shaped ceramic part with additional paste after step c) and before step d).

10. A method according to claim 1, wherein a set of pre-shaped ceramic parts is produced having different shades of color and wherein the pre-shaped ceramic part is selected from the set so as to match substantially the color of the dental replacement.

11. A method according to claim 10, wherein the pre-shaped ceramic part is selected to be more translucent or lighter than the dental replacement.

12. A method according to claim 1, wherein the pre-shaped ceramic part comprises 40–90% of the volume of material to be placed onto the dental support structure on the labial or buccal side.

13. A method according to claim 12, wherein the pre-shaped ceramic part comprises 70% of the volume of material to be placed onto the dental support structure on the labial or buccal side.

14. A method according to claim 1, wherein the pre-shaped ceramic part has a planar inner side facing the dental replacement in order to prevent air inclusions and wherein the inner side is roughened to ensure a safe connection of the pre-shaped ceramic part to the dental support structure during firing.

15. A method according to claim 1, wherein the pre-shaped ceramic part is comprised of at least one layer and has a translucence matching the translucence of a natural tooth.

16. A method according to claim 15, wherein said pre-shaped ceramic part is comprised of two layers.

17. A dental replacement comprising a dental support structure having a labial or buccal side, a ceramic paste, and a fired, pre-shaped ceramic part connected to the labial or buccal side of the dental support by being at least partially embedded in the ceramic paste, the fired, pre-shaped ceramic part, the ceramic paste, and the dental support structure having been fired together after the fired-preshaped ceramic part has been imbedded in the paste on the support.

18. A dental replacement according to claim 17, wherein said pre-shaped ceramic part is comprised of two layers and is premanufactured whereby the labial or buccal layer is more translucent than the lingual layer.

19. A dental replacement according to claim 17, wherein said pre-shaped ceramic part has a cervical area and wherein said cervical area is slanted at an angle of 15° to 75° relative to a labial surface of the dental replacement and wherein the cervical area is covered by the ceramic paste.

* * * * *